United States Patent [19]
Bousfield et al.

[11] Patent Number: 6,050,139
[45] Date of Patent: Apr. 18, 2000

[54] DEVICES AND METHODS FOR TESTING TACK UNIFORMITY OF A COATING ON A SUBSTRATE

[75] Inventors: Douglas W. Bousfield, Glenburn; Phillip S. Coleman, Standish; John C. Hassler, Orono; Alonzo K. Osgood, Portland, all of Me.

[73] Assignee: S. D. Warren Services Company, Westbrook, Me.

[21] Appl. No.: 09/056,352

[22] Filed: Apr. 7, 1998

[51] Int. Cl.[7] .......................... G01B 21/08; G01H 17/00
[52] U.S. Cl. .......................... 73/150 A; 73/150 R
[58] Field of Search .............. 73/150 A, 150 R

[56] References Cited

U.S. PATENT DOCUMENTS

| | | | |
|---|---|---|---|
| 3,531,986 | 10/1970 | Van Gastel | 73/150 |
| 3,559,475 | 2/1971 | Dillon et al. | 73/150 |
| 3,741,012 | 6/1973 | Day | 73/150 |
| 4,114,434 | 9/1978 | Hauser | 73/150 |
| 4,856,326 | 8/1989 | Tsukamoto | 73/150 |
| 4,934,185 | 6/1990 | Nishiyama et al. | 73/105 |
| 4,958,521 | 9/1990 | Morimoto et al. | 73/827 |
| 5,168,752 | 12/1992 | Konermann et al. | 73/150 |
| 5,673,586 | 10/1997 | Mann | 73/150 |

OTHER PUBLICATIONS

Tack Development: An Analysis of Ink/Paper Interaction in Offset Printing, 1994 Coating Conference, TAPPi Proceedings, pp. 243–260.

A Method for Measuring Tack Build of Offset Printing Inks on Coated Paper, by P. W. Concannon et al., S.D. Warren Company, pp. 1–20 (date not available).

Ink Tack—Part 3: Surface Measurement, by N. Plowman, Graphic Arts Monthly, Jun. 1989.

Direct Measurement of Tensile Stress (tack) in Thin Ink Films, Y.H. Zang et al., The Society of Rheology, Inc., 1991, pp. 345–361.

Primary Examiner—Hezron Williams
Assistant Examiner—Jay L. Politzer
Attorney, Agent, or Firm—Fish & Richardson P.C.

[57] ABSTRACT

Devices and methods are provided to characterize local, small-scale variations in tack build-up, e.g., by measuring tack over areas smaller than 20 mm$^2$, preferably over areas smaller than 1 mm$^2$. These devices and methods measure the tack properties, e.g., tack build-up, of a coating over a very small area, allowing characterization of such small-scale variations. The invention also provides methods for using such characterization to predict back trap mottle (BTM).

32 Claims, 4 Drawing Sheets

DEVICES AND METHODS FOR TESTING TACK UNIFORMITY OF A COATING ON A SUBSTRATE

BACKGROUND OF THE INVENTION

The present invention relates to devices and methods for testing tack uniformity of a coating on a substrate. The term "coating", as used herein, is intended to refer to any liquid that is applied to a substrate, including both inks and non-ink coatings. Substrates include coated and non-coated papers, and other coated and non-coated sheet materials.

Tack is one of the most important characteristics of coatings, affecting, for example, the runnability and printability of papers. Tack does not remain constant after a coating is applied, but instead changes over time as the coating consolidates, interacts with the paper surface, and dries. The change in tack as a function of time is generally referred to as "tack build-up". In multi-color offset printing, tack build-up of inks is important both to ink-setting and to the transfer of additional ink film to the fresh ink layers already on the paper. Part of the fresh ink already on the paper may retransfer or "backtrap" to subsequent printing blankets. If the tack build-up is not uniform over the paper surface, the local transfer/retransfer balance is upset and the resulting print will not be uniform and may appear mottled. This partial or uneven setting of the ink on a microscale is referred to as "backtrap mottle" (BTM), and can result in an unacceptable blotchy or mottled printed surface with alternating light and dark printed areas. The size of the light and dark areas varying in print density are a distinguishing characteristic of a given printed substrate. Generally, BTM is more noticeable and objectionable for larger printed areas, smaller halftones, coarser BTM patterns, and larger spacings of the light and dark areas. BTM can be measured by commercially available instruments or by subjective expert evaluation.

There is often a need in the paper-making, coating and printing industries to measure tack properties, such as tack build-up, so that BTM and other production problems can be predicted and minimized. As a result, a number of devices have been developed to measure tack build-up. Typically, these devices integrate over a large area, so that the presence of small-scale (less than 20 mm$^2$) areas of non-uniform (slower or faster) tack build-up may not be detected.

SUMMARY OF THE INVENTION

The inventors have found that, in order to accurately predict BTM and other problems resulting from non-uniform tack build-up, it is important to characterize local, smallscale variations in tack build-up, e.g., by measuring tack over areas smaller than 20 mm$^2$, preferably over areas smaller than 1 mm$^2$. The present invention provides devices and methods for measuring the tack properties, e.g., tack build-up, of a coating over a very small area, allowing characterization of such small-scale variations. The invention also provides methods for using such characterization to predict BTM.

In one aspect, the invention features a method of testing the tack build-up of a coating on a substrate. The method includes (a) providing a test substrate; (b) applying a coating sample to a portion of the test substrate; (c) contacting the portion of the test substrate with a probe having a contact area of less than about 20 mm$^2$; (d) removing the probe from the coated portion; and (e) measuring a parameter relating to the movement of the probe as it is being removed, to determine the tack of the coating sample. The phrase "contact area", as used herein, means the portion of the probe which contacts the substrate during the contacting step.

Preferred methods include one or more of the following features. Steps (c) through (e) are repeated a plurality of times. The test substrate is a coated paper and the coating sample is an ink. The contact area is less than about 10 mm$^2$, more preferably less than about 5 2 mm$^2$, and most preferably less than about 1 mm$^2$. The measured parameter is the maximum deflection of a biasing element associated with the probe by the probe at the moment that the probe is released from the substrate. The biasing element is a leaf spring. The deflection is measured by an LVDT. The probe is a ferromagnetic material, and the measured parameter is the current applied to an electromagnet that is positioned to move the probe away from the substrate when current is applied to the electromagnet. The applying step includes applying said coating sample to said probe and contacting said test substrate with said probe to transfer said coating from said probe to said substrate. The applying step and contacting step are performed simultaneously.

In another aspect, the invention features a method of testing variation in the tack build-up of a coating on a substrate. The method includes (a) providing a test substrate; (b) contacting a portion of the test substrate with a coating sample to coat said portion; (c) contacting the coated portion with a probe; (d) removing the probe from the coated portion; (e) measuring a parameter associated with the removal of the probe from the coated portion; and (f) repeating steps (b)–(e) a plurality of times at each of a plurality of locations on the surface of the test substrate to determine the variation in tack build-up over the surface of the test substrate.

In another aspect, the invention features a device for testing the tack build-up of a coating on a substrate. The device includes (a) a probe constructed to be movable between a position in which it contacts the substrate and a position spaced from the substrate, and having a contact surface for contacting a portion of the substrate, the contact surface having an area of less than about 20 mm$^2$, (b) an activation device constructed to move the probe between its positions, and (c) a measurement device constructed to measure a parameter associated with the force required to remove the probe from the substrate after it has contacted the substrate.

Preferred devices include one or more of the following features. The area of the contact surface is less than about 10 mm$^2$, more preferably less than about 5 mm$^2$, and most preferably less than about 1 mm$^2$. In one embodiment, the device further includes a biasing element, e.g., a leaf spring, associated with the probe, constructed to be deflected as the probe is being moved to its spaced position by the force exerted by the coating on the probe. The measurement device is constructed to detect and measure the deflection of the biasing element, and is preferably an LVDT. The activation device includes a motor. The device further includes a computer to control movement of the probe. In another embodiment, the device further includes an electromagnet positioned above the probe, and the probe is moved to its contact position when no current is supplied to the electromagnet, and moved to its spaced position by magnetic force, when current is supplied to the electromagnet. In this embodiment, the measuring device includes a light source and photosensor, positioned on opposite sides of the probe to detect the moment when the probe breaks free of the substrate, as the probe is being moved from the contact to the spaced position. Thus, the measuring device measures the current applied to the electromagnet at the point at which the probe breaks free of the substrate.

The invention also features methods for predicting or evaluating the backtrap mottle of a particular ink/substrate combination. A preferred method includes measuring the variation in tack build-up of the ink on the substrate at a plurality of locations, each location having an area of less than about 20 mm².

Other features and advantages of the invention will be apparent from the following detailed description, the drawings, and the claims.

DETAILED DESCRIPTION OF PREFERRED EMBODIMENTS

Test Methods and Devices

Figure 1:
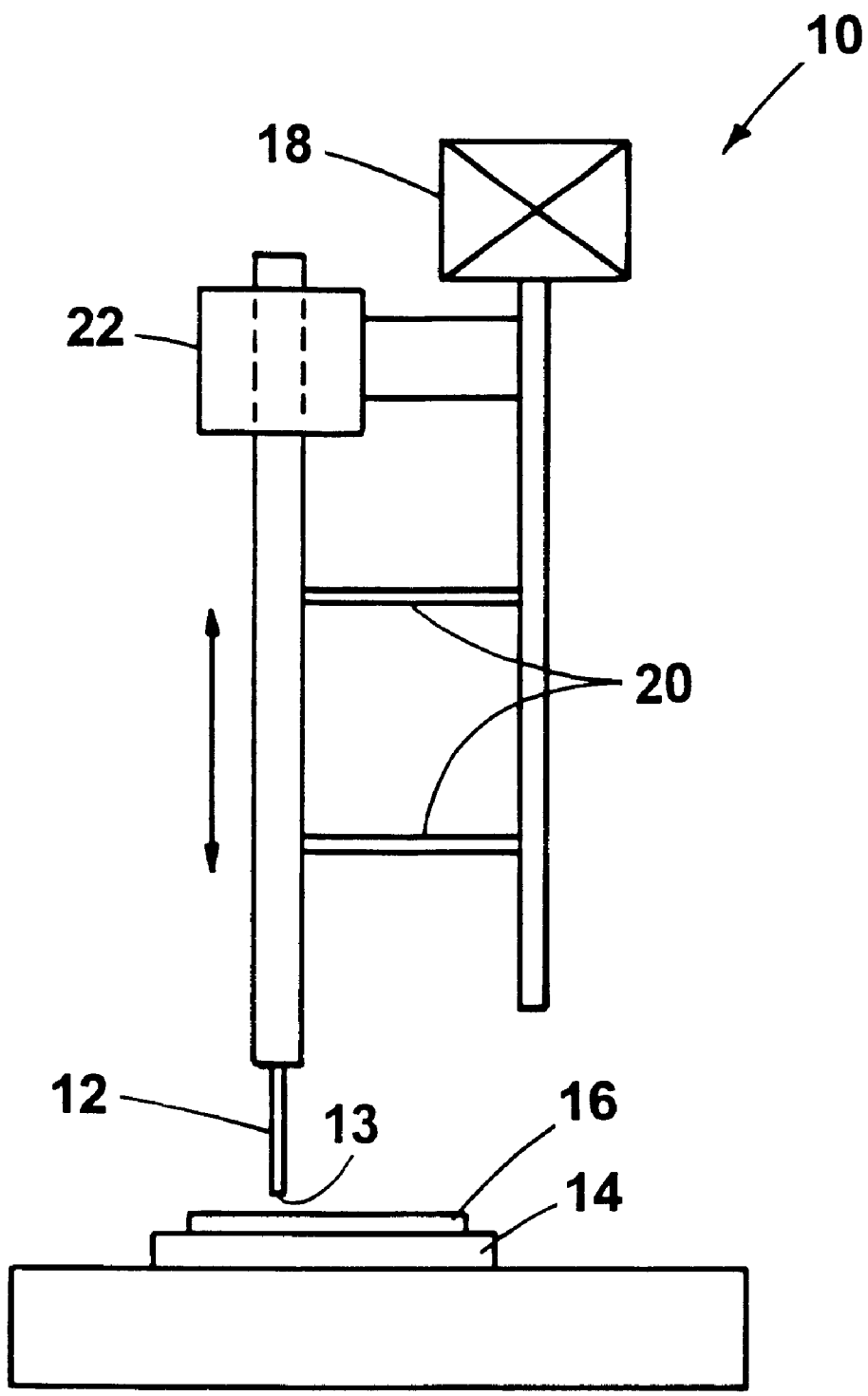
FIG. 1 is a schematic side view of a device for measuring tack build-up according to one embodiment of the invention.

Referring to FIG. 1, a device 10 for measuring tack build-up includes a probe 12 for contacting a paper substrate, and a sample holder 14. At the start of a test, a smooth plastic film, e.g., a Mylar plastic film, having a layer of ink on its surface, is placed in sample holder 14. Probe 12 is then brought into contact with the plastic film to apply an ink layer to the base 13 of the probe. A paper test substrate 16 is placed next to the plastic film in the sample holder 14, and sample holder 14 is moved in the x-y direction until the paper test substrate 16 is positioned under the probe 12. The sample holder can be moved manually, or a motor can be provided to move the holder automatically.

The probe 12 is then moved up and down repeatedly so that it contacts the paper substrate 16 a number of times over a predetermined period of time. Depending on what tack property is to be tested, the probe can contact the substrate in the same place each time, a different place each time, or a combination of same and different areas. If it is desired that the probe contact different areas, this can be accomplished by moving the sample holder in the x-y plane. In some instances, e.g., when uniformity of tack build-up is being measured, to have the probe contact the substrate in a predetermined pattern that is selected to detect small-scale nonuniformity. Preferably, the probe contacts the substrate at a plurality of locations in each of the machine and cross-machine directions. The spacing of the test locations should typically be at least 1 cm, to minimize the effect of ink solvent absorption at one test location on an adjacent test location. One method of determining the desired spacing is to print a six-color sheetfed printing press print using the same substrate/coating combination, measure the distance between light and dark areas of the press print, calculate the average distance, select an odd number as a factor, multiply this by the average distance, and use the result as the test spacing. Good results have been obtained using a total test area of from about 100 to 500 cm², and a test spacing of 1–3 cm in the machine and cross-machine directions.

The probe 12 is moved at a predetermined speed, preferably greater than 15 mm/min, by a motor 18. The force required to pull the inked probe away from the paper surface after each contact is proportional to the deflection of leaf spring 20, and is measured by a linear variable differential transformer (LVDT) 22. A computer (not shown) controls the motor 18 and records the output of LVDT 22. When the computer detects that the LVDT output signal has reached zero, the direction of the motor - and thus the direction of movement of the probe—is reversed.

Figure 2:
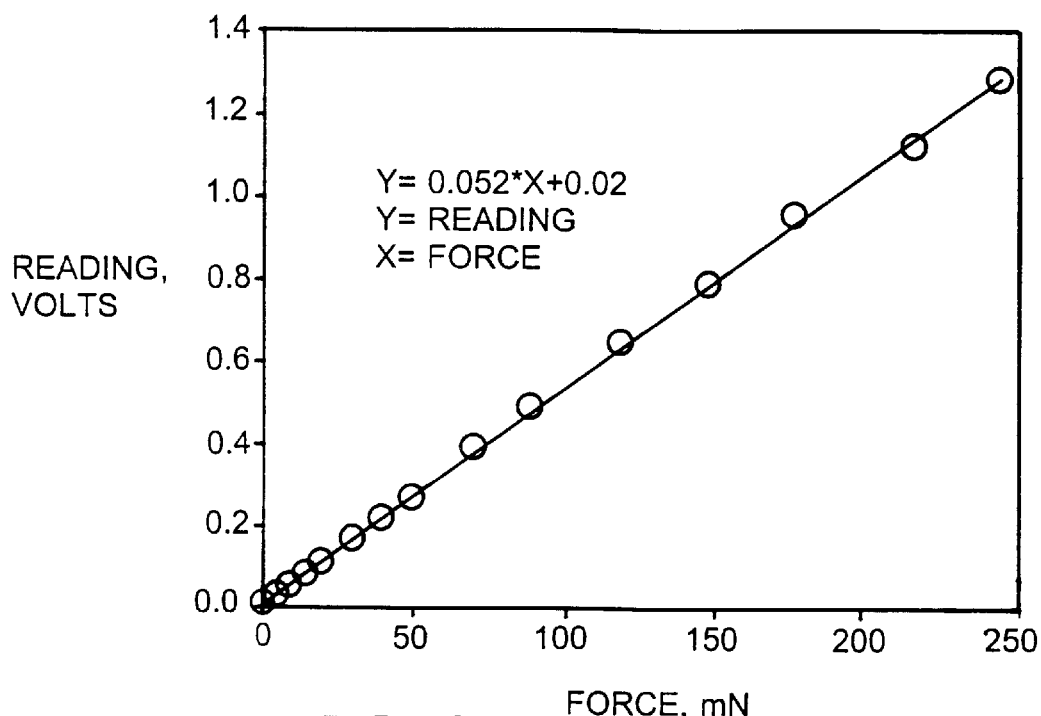
FIG. 2 is a graph showing an example of a calibration curve for a device of FIG. 1.

A single up/down cycle of the probe 12 proceeds as follows. At the start of the cycle, the LVDT 22 reads zero, reflecting the zero deflection of the leaf spring 20. As the probe moves downward the motor also moves the LVDT 22 and leaf spring 20 downward simultaneously, until the prove deflects upward upon contacting the paper substrate. Downward movement is stopped by the motor when the LVDT 22 outputs a predetermined "load voltage", indicating that the probe has contacted the paper surface with a known, predetermined force. Once this output has occurred, the computer reverses the motor and runs it upward until the probe breaks away from the paper substrate. The maximum deflection of the probe downward before it breaks away is recorded by the computer and is taken as the tack value. By calibrating the device 10 with a series of analytical weights, the raw voltage output of the LVDT can be converted to a measurement of absolute force. A sample calibration curve for device 10 is shown in FIG. 2.

This up/down cycle of the probe is repeated at predetermined intervals, e.g., 1–10 seconds between contacts, for a predetermined period of time, so that the change in tack value over time can be recorded and graphed to show the tack build-up, on a micro-scale, over a small area for a given paper/ink combination. The test can also be repeated at several locations within a particular sample substrate, to determine the variation in tack build-up over the surface of the substrate. The contact pressure of the probe and duration of contact can be adjusted by the user of device 10. These parameters will be adjusted for a given test situation depending on the coating and substrate to be tested. Preferably, sufficient force is applied to achieve wetting and measurable separation, but the force is not so great that the probe drives the coating into the substrate. For most coating/substrate combinations, a contact force of from 1–100 mN and a contact duration of from 0.1 to 1 second will produce accurate results.

Different paper test substrates can be tested using a particular ink, and the measured tack build-up can be correlated with the BTM observed for the same paper/ink combinations. Generally, the higher the variation in the rate of tack build-up over the surface of the substrate, the worse the BTM will be. Thus, testing the variation in tack build-up using the above-described method can be used to predict the BTM for a given paper/ink combination.

If desired, tack build-up can also be measured on a non-paper control sample, e.g., an inked Mylar plastic film, for comparison with the results obtained using paper test substrates. This control measurement can be used to measure the tack build-up that is caused by factors other than the surface characteristics of a porous substrate, e.g., solvent evaporation and test parameters.

Figure 5:
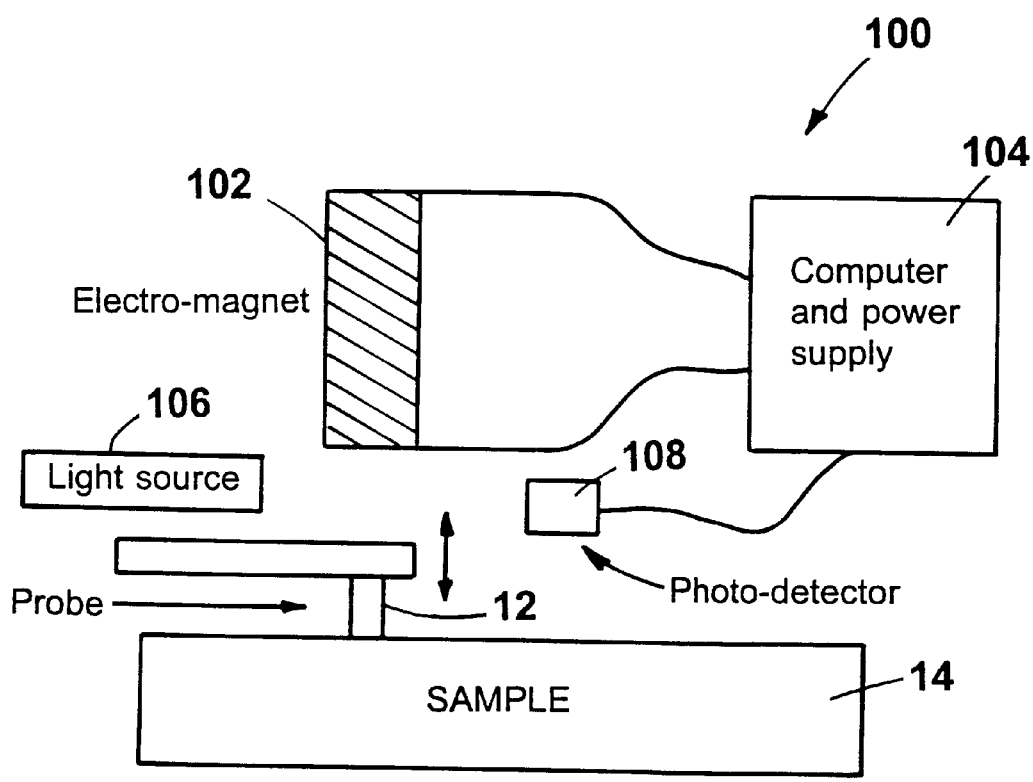
FIG. 5 is a schematic side view of a device for measuring tack build-up according to an alternate embodiment of the invention.

Referring to FIG. 5, an alternate device 100 is shown. Like device 10, described above, device 100 includes a probe 12 for contacting a paper substrate, and a sample holder 14. The probe is inked and used for testing tack build-up in the same manner described above, except for the manner in which the probe is moved and the parameter that is measured when the probe is moved upward after contacting the substrate. Device 100 moves the probe between its raised and lowered positions using magnetic force, rather than a motor. Thus, device 100 includes an electromagnet 102 that is electrically connected to a computer-controlled power source 104. The probe is held in its raised position by the magnetic force that is generated when current is applied to the electromagnet 102. When the probe is to be lowered, the current is turned off, and the weight of the probe causes the probe to drop to its lowered position. The force applied by the probe to the substrate will be the weight of the probe. Once the probe has contacted the substrate, current is applied to the electromagnet, and increased until the probe breaks away from the substrate surface. The moment at which the probe breaks away is detected by a light source 106 and a photo-detector 108. The light source and photo-detector are positioned on opposite sides of the probe, at a predetermined height from the substrate, so that when the probe breaks away the probe passes between the light source and photo-detector, causing the photo-detector to change voltage. The current is measured at the moment at which the photo-detector changes voltage, and this current measurement can then be converted to the force that was required to pull the probe away from the substrate (in the same manner that the LVDT reading is converted).

Materials

Probe 12 is preferably a small diameter rod, having a diameter of less than 5 mm. Preferred probes have diameters of 1 mm or less. Probe 12 is preferably made of metal, but may be made of other impermeable materials that will not interact with the ink or coating to be tested. In the embodiment shown in FIG. 5, the probe has ferromagnetic properties sufficient to allow it to be raised by the magnetic force exerted by the electromagnet.

Suitable LVDTs can be readily determined. One suitable LVDT is Model No. E50, commercially available from Lucas Control System Products, 1000 Lucas Way, Hampton, Va. 23666.

Any small motor capable of operating under the conditions described above may be used. One suitable motor is Model GBC 35DH, manufactured by Soho Company.

A suitable leaf spring may be constructed by cutting a 1" by 1" piece from a 1/8 inch steel sheet.

The source code, written in BASIC, for the software used by the computer is attached as Appendix A.

EXAMPLE

Two ink samples were used, both cyan inks: (1) a proofing and mottling test ink commercially available from Michael Huber Munchen GmbH; and (2) a quick set offset ink commercially available from Flint Ink, Inc. under the tradename Capiplus III Process Cyan.

Test papers were produced on a pilot coater at S. D. Warren, using the following procedure: The base stock was a 150 g/m$^2$ ground-wood free cover stock with typical northern mill pulp furnish, blade coated with 22 g/m$^2$ coat weight per side, dried with a designed combination of infrared, early air foil and late air foil drying to a moisture of 6.0% and on-line finished with soft-nip calendering. The coating consisted of 50 parts #1 high brightness clay, 10 parts calcined clay, 40 parts ultrafine ground limestone (UFGL), 14 parts 1800 Å styrene butadiene latex, 2 parts ethylated starch, and conventional additives, and was applied to the paper by coating on the wire-side on day one at the experimental design's drying centerpoint, and coating on the functional/experimental felt-side on day two. The wire-side process variables and end-product attributes were all within statistical process control (SPC). Likewise, for the feltside, all non-drying process variables were in SPC and the end-product attributes were essentially indistinguishable except for print quality (BTM).

To test the small-scale variation in tack build-up of each ink/paper combination, the following procedure was used. The entire procedure was carried out in a temperature/humidity controlled room at 23° C. and 50% relative humidity. First, a predetermined quantity (16.50 g/m 2) of ink was applied to a Mylar plastic film, using an IGT AIC2-5 printability tester with a Westvaco rod applicator attachment. The test paper and the inked Mylar film were attached to the sample holder (a smooth metal block) using double-sided tape. Using a testing device as described above in the Test Method & Device section, a 1.1 mm diameter probe contacted the Mylar film with a force of 25 mN to apply ink to the probe. The probe then contacted the test paper in the same location 40 times, at 7 second intervals, with a force of 25 mN, to measure the change in ink tack over time. This test procedure was used on each ink/test paper combination at 15–20 different locations on each test paper, to measure variation in tack build-up over the surface of each test paper.

The entire test was also performed using a 2.2 mm diameter probe in place of the 1.1 mm diameter probe.

A graph of the multiple tack forces measured at the different locations on each test paper versus elapsed time was generated for each ink/test paper combination and probe diameter, and was used to determine rate of tack build-up and interpret the ink/paper interaction. The above-described test was also performed for each ink using the Mylar plastic film as the test substrate, as a control.

Figure 3:
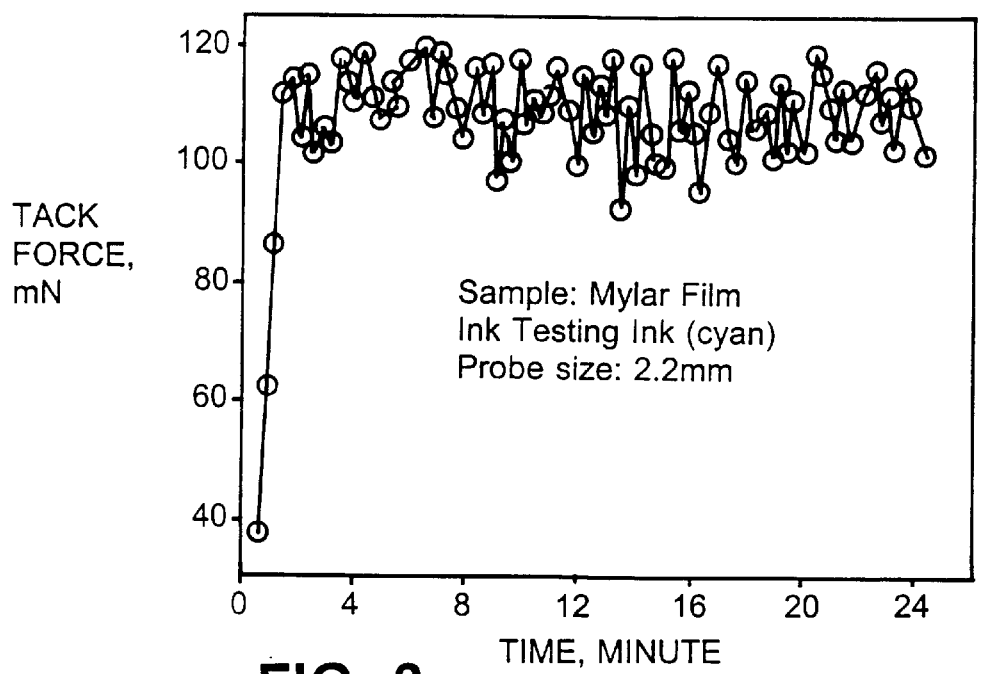
FIGS. 3 and 4 are graphs showing the change in ink tack force as a function of time (tack build-up) for various ink/substrate combinations.
Figure 4:
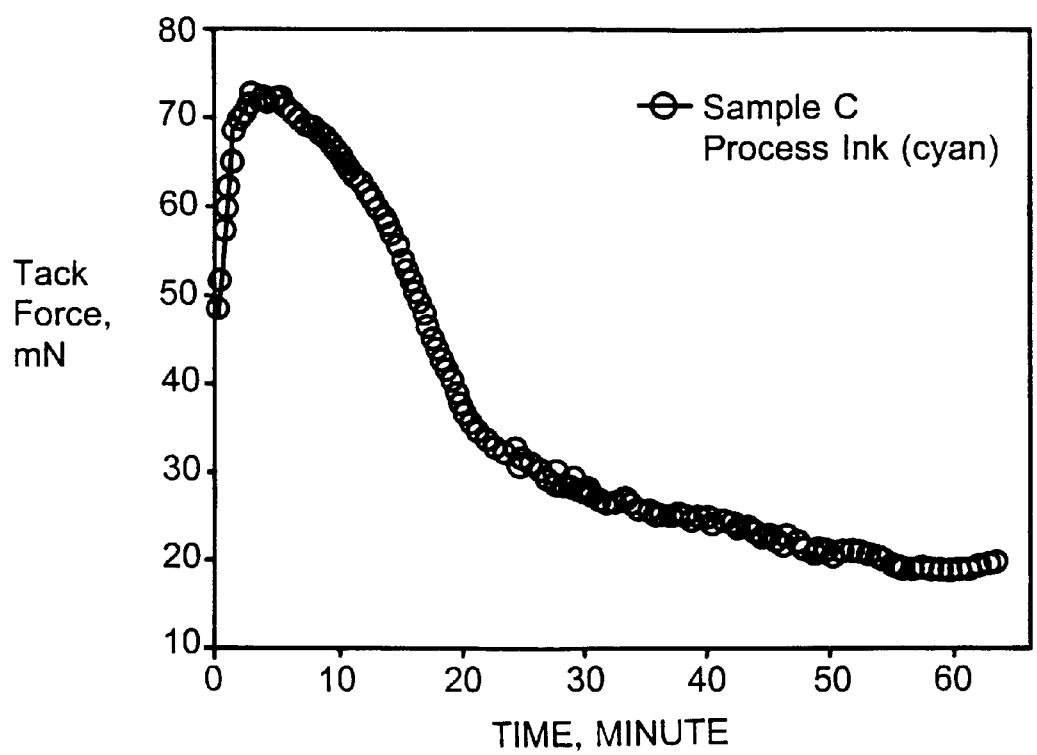

The results of the tack build-up control test on the Mylar film, using a 2.2 mm probe, are shown in FIG. 3. After a rapid initial increase in tack force, the tack force of the ink on Mylar film remained constant over an extended period of time. FIG. 4 shows one of the graphs obtained for a particular ink/test paper combination. As shown in FIG. 4, after the ink contacted the coated paper, tack build-up was rapid. After the first eighty seconds, the tack force reached a plateau and started to decrease. Another plateau in tack build-up was reached in about an hour. The tack force dynamics were observed to be quite different between samples.

To study the correlation between tack build-up and BTM, eight coated papers with very similar optical and print end-product attributes, but with different degrees of print mottle, were tested using the above-described procedure. Table 1 shows the basic properties of these papers. Table 2 reports, for each sample, (a) the coefficient of variation in both first point tack force and initial rate of tack build-up, measured with each probe (1.1 mm and 2.2 mm), and (b) a subjective evaluation of BTM. The BTM subjective rating is based on the degree of BTM after printing these samples on a six-color offset press, and was ranked by a panel of experts at S. D. Warren on a traditional 1–5 BTM scale (1=low BTM, 5=highest BTM). As calculated from the data in Table 2, the squared correlation coefficient ($r^2$) between the coefficient of variation for the rate of tack build-up and the BTM was better for the 1.1 mm probe ($r^2$ =0.87) than for the 2.2 mm probe ($r^2$ =0.13), indicating that BTM can be best predicted by measuring tack build-up over a very small area. Correlation with BTM was also generally better for initial rate of tack build-up than for first point tack force. Interestingly, none of the other properties of the paper samples that are shown in Table 1 appear to have any correlation with BTM.

TABLE 1

| Sample | Brightness (%) | PPS-10kg-soft (μm) | 75° Paper Gloss (%) | 75° Heatset Ink Gloss (%) | Tobias Microgloss |
|---|---|---|---|---|---|
| A | 78.6 | 1.32 | 62.6 | 85.8 | 742 |
| B | 78.4 | 1.20 | 67.6 | 89.0 | 809 |
| C | 79.7 | 1.19 | 62.5 | 90.0 | 741 |
| D | 78.9 | 1.36 | 60.7 | 86.1 | 754 |
| E | 79.7 | 1.23 | 63.0 | 90.0 | 726 |
| F | 79.5 | 1.35 | 60.0 | 88.9 | 710 |
| G | 79.4 | 1.30 | 63.2 | 86.0 | 894 |
| H | 79.6 | 1.35 | 61.8 | 88.1 | 772 |

TABLE 2

| Sample | 1.1 mm 1st Point Tack Coefficient of Variation | 2.2 mm 1st Point Tack Coefficient of Variation | 2.2 mm Coefficient of Variation of Rate of Tack Buildup | 1.1 mm Coefficient of Variation of Rate of Tack Buildup | BTM Expert Rating |
|---|---|---|---|---|---|
| A | 0.239 | 0.278 | 0.487 | 0.286 | 1.5 |
| B | 0.231 | 0.322 | 0.630 | 0.295 | 1 |
| C | 0.244 | 0.328 | 0.652 | 0.407 | 2 |
| D | 0.302 | 0.284 | 0.527 | 0.471 | 4 |
| E | 0.256 | 0.380 | 0.706 | 0.465 | 3 |
| F | 0.317 | 0.326 | 0.664 | 0.369 | 3 |
| G | 0.330 | 0.300 | 0.663 | 0.535 | 5 |
| H | 0.333 | 0.354 | 0.707 | 0.586 | 5 |

Other embodiments are within the claims. For example, while the preferred test method and device described has been described with reference to testing tack build-up of an ink on a paper substrate, the devices and methods of the invention may be used to test the tack build-up of other coatings on other types of substrates. Other suitable coatings and substrates include but are not limited to size press and coatings on various bodystocks, and varnishes, solvents or oils on coated paper and/or on ink films. Moreover, while the devices described above have utilized leaf springs and magnetic force to bias the probe, other biasing elements may be used.

APPENDIX A

```
DECLARE SUB motor (outval1%, outval2%)
DECLARE SUB loadup (loadvolts!)
DECLARE FUNCTION setzero! ()
DECLARE FUNCTION vmax! ()
DECLARE FUNCTION voltsin! (chno%)
REM ++++++++++++++++++++++++++++++
REM       T A C K x x . B A S
REM
REM     Author: J. C. Hassler
REM     Date:   6-Aug-96
REM
REM     Abstract: Program to measure the
REM             time dependent tack of ink.
REM             Assumes a CIO-DAS08-AOH board.
REM     V.2.00 (4/8/97) New motor control, uses
REM             D/A and PA26 op amp.
REM --------------------------------
COMMON SHARED bse%, bp1%, bp2%, bp3%, bp8%, bp9%
COMMON SHARED bp10%, bp11%, mot0%, mot1%, nchar$
    bse% = &H300
    bp1% = bse% + 1
    bp2% = bse% + 2
    bp3% = bse% + 3
    bp8% = bse% + 8    ' DAC0 Low
    bp9% = bse% + 9    ' DAC0 High (uses low nybble)
    bp10% = bse% + 10  ' DAC1 Low
    bp11% = bse% + 11  ' DAC1 High
```

APPENDIX A-continued

```
    mot0% = 0
    mot1% = 3095
    CALL motor(mot0%, mot0%)   ' motor off
    OUT bp3%, 0     ' set to +/- 5 volts a/d
    PRINT "TACK Version 2.00   4-Aug-97"

' -.-.-.-.-.-.-.-.- OPEN FILE -.-.-.-.-.-.-.-.-.-.-.-.-.-.
REM This block checks before opening the output data file, to avoid
REM overwriting existing data.
    ON ERROR GOTO notexist      ' begfn error trapping
getname:
    INPUT "Enter name of file for data:"; outfil$
    OPEN outfil$ FOR INPUT AS #1   ' check to see if it exists
    CLOSE # 1                       ' no error, so file does exist INPUT "Data file exists; Overwrite? [y/n]"; yn$
    IF yn$ <> "Y" AND yn$ <> "y" THEN
        GOTO getname ' get another name
    ELSE
        GOTO doopen                ' Overwrite the file
    ENDIF notexist:
REM If the file does not exist, we arrive here, and just return
REM to open the file. (Error number 53 on line number 100.)
    IF ERR = 53 AND ERL = 100 THEN RESUME doopen
    ON ERROR GOTO 0      ' handles any other error, and stops.

doopen:                          ' do the file-open
    ON ERROR GOTO 0              ' stop error trapping
    OPEN outfil$ FOR OUTPUT AS #1
' -.-.-.-.-.-.-.-.-.- END of OPEN -.-.-.-.-.-.-.-.-.-.-.-.
INPUT "Enter one line of information for the data file:"; titles$
PRINT #1, titles$
CLOSE #1              ' will re-open for APPEND when we need it.

PRINT "Type U for up, D for down, G to start measurements."
    PRINT " Any other key to stop."
    tstart = TIMER
I1:
    nchar$ = INKEY$
    IF nchar$ = "" THEN GOTO I1
    IF nchar$ = "G" OR nchar$ = "g" THEN GOTO I2 ELSE GOTO setmotor I2:
    nchar$ = ""
    SLEEP (2)                ' wait for bouncing to stop
    vzero = setzero
    CALL loadup(-.5)
    IF nchar$ <> "" THEN GOTO setmotor
    volts = vmax
    IF nchar$ <> "" THEN GOTO setmotor
    dtime = TIMER - tstart
    PRINT dtime, volts - vzero, vzero
    OPEN outfil$ FOR APPEND AS #1
    PRINT #1, dtime, volts - vzero, vzero
    CLOSE #1
    GOTO I2 setmotor:
    IF nchar$ = "U" OR nchar$ = "u" THEN
        CALL motor(mot0%, mot1%)
    ELSEIF nchar$ = "D" OR nchar$ = "d" THEN
        CALL motor(mot1%, mot0%)
    ELSE
        CALL motor(mot0%, mot0%) ' any other char = stop
    END IF
        GOTO I1

SUB loadup (loadvolts)
    CALL motor(mot1%, mot0%)      ' start down motion
sI1:
    nchar$ = INKEY$
    IF nchar$ <> 0 "" THEN EXIT SUB
    volts = voltsin(0)
    IF volts > loadvolts THEN GOTO sI1
    CALL motor(mot0%, mot0%)      ' Stop motor
END SUB
```

APPENDIX A-continued

```
SUB motor (outval1%, outval2%)
    temp1% = outval1% AND &HFF
    temp2% = (outval1% AND &HF00) \ 256
    OUT bp8%, temp1%
    OUT bp9%, temp2%
    temp1% = outval2% AND &HFF
    temp2% = (outval2% AND &HF00) \ 256
    OUT bp10%, temp1%
    OUT bp11%, temp2%
END SUB FUNCTION setzero
    vzero = 0
    FOR i = 1 TO 300
    vzero = vzero + voltsin(0)
    NEXT i
    setzero = vzero / 300
END FUNCTION FUNCTION vmax
    cmax = 100
    CALL motor(mot0%, mot1%)  ' set motor for upwards
    SLEEP (1)
    vmaxx = -10
lm1:
    vin = voltsin(0)
    IF vin > vmaxx THEN
        vmaxx = vin
        count = 0
    ELSE
        count = count + 1
    END IF
    nchar$ = INKEY$
    IF nchar$ <> "" THEN EXIT FUNCTION
    IF count < cmax THEN GOTO lm1
    CALL motor(mot0%, mot0%)  ' stop motor
    vmax = vmaxx
END FUNCTION FUNCTION voltsin (chno%)
    OUT bp2%, chno%   ' set up channel number
    OUT bp1%, 0  ' start A/D
bsy:
    IF (INP(bp2%) AND &H80) <> 0 THEN GOTO bsy
    hib% = INP(bp1%)
    Iob% = INP(bse%)
    tmp1% = (hib% AND &HF) * 16
    tmp1% = tmp1% OR ((Iob% AND &HF0) \ 16)
    tmp2% = (hib% AND &HF0) \ 16
    num% = (hib% AND &HFF) * 16 + (Iob% AND &HF0) / 16
    REM ****************************
    REM change this line to match the a/d board we are using:
    voltsin = num% * 10! / 4096! - 5
    'PRINT USING " ##.#### ";volts
END FUNCTION
```

What is claimed is:

1. A method of testing tack properties of a coating on a substrate comprising:
   (a) providing a substrate;
   (b) applying a coating sample to a portion of the substrate, said coating sample on said substrate exhibiting local variations in tack;
   (c) contacting the portion of the substrate with a probe having a contact area of less than 20 mm$^2$, the surface area of the probe being smaller than the scale of local variations in tack of the coating sample;
   (d) removing the probe from the coated portion;
   (e) measuring a parameter relating to the movement of the probe as it is being removed, to determine the tack of the coating sample; and
   (f) repeating steps (c)–(e) to measure the change in tackiness as a function of time and the tack uniformity of the coating sample.

2. The method of claim 1 wherein steps (c) through (e) are repeated a plurality of times.

3. The method of claim 1 wherein said substrate is a coated paper and said coating sample is an ink.

4. The method of claim 1 wherein said contact area is less than about 10 mm$^2$.

5. The method of claim 1 wherein said contact area is less than about 5 mm$^2$.

6. The method of claim 1 wherein said contact area is less than about 1 mm$^2$.

7. The method of claim 1 wherein said parameter is the maximum deflection of a biasing element associated with the probe by the probe at the moment that the probe is released from the substrate.

8. The method of claim 7 wherein said biasing element is a leaf spring.

9. The method of claim 7 wherein said deflection is measured by an LVDT.

10. The method of claim 1 wherein said applying step includes applying said coating sample to said probe and contacting said substrate with said probe to transfer said coating from said probe to said substrate.

11. The method of claim 10 wherein said applying step and contacting step are performed simultaneously.

12. The method of claim 1 wherein the probe is a ferromagnetic material, and the measured parameter is the current applied to an electromagnet that is positioned to move the probe away from the substrate when current is applied to the electromagnet.

13. A method of testing tack properties of a coating on a substrate comprising:
   (a) contacting a portion of a substrate with a coating sample to coat said portion;
   (b) contacting the coated portion with a probe;
   (c) removing the probe from the coated portion;
   (d) measuring a parameter associated with the removal of the probe from the coated portion;
   (e) repeating steps (b)–(d) a plurality of times at each of a plurality of locations on the surface of the substrate, the locations being spaced a predetermined distance apart; and
   (g) prior to steps (a)–(e), determining said predetermined distance by the following steps:
      (i) printing a printing press print using the same type of substrate and coating used in steps (a)–(f);
      (ii) measuring the distances between light and dark areas of the printing press print at a plurality of positions on the printing press print and calculating the average of these distances;
      (iii) selecting an odd number as a factor; and
      (iv) multiplying said factor by said average distance, the product of this multiplication being said predetermined distance.

14. A method of testing tack properties of a coating on a substrate comprising:
   (a) providing a substrate;
   (b) contacting a portion of the substrate with a coating sample to coat said portion, said coating sample on said substrate exhibiting local variations in tack;
   (c) contacting the coated portion with a probe, the surface area of the probe being smaller than the scale of local variations in tack of the coating sample;
   (d) removing the probe from the coated portion;
   (e) measuring a parameter associated with the removal of the probe from the coated portion; and (f) repeating steps (c)–(e) a plurality of times at each of a plurality of locations on the surface of the substrate to measure the change in tackiness as a function of time and the tack uniformity of the coating sample, and thereby to determine the variation in tack build-up over the surface of the substrate.

15. The method of claim 1 wherein said coating sample is an ink.

16. The method of claim 14 wherein said coating sample is an ink.

17. The method of claim 14 wherein said substrate is a coated paper.

18. The method of claim 14 wherein said contact area is less than about 10 mm$^2$.

19. The method of claim 14 wherein said contact area is less than about 5 mm$^2$.

20. A device for testing the tack uniformity and change in tack as a function of time of a coating sample on a substrate, the coating sample exhibiting local variations in tack, the device comprising:

a probe constructed to be repeatedly movable between a position in which it contacts the substrate and a position spaced from the substrate, and having a contact surface for contacting a portion of the substrate, the contact surface having an area of less than about 20 mm$^2$, the surface area of the probe being smaller than the scale of local variations in tack of the coating sample;

an activation device constructed to repeatedly move the probe between its positions to cause the probe to contact the substrate a plurality of times at each of a plurality of locations on the surface of the substrate to measure the change in tackiness as a function of time and the tack uniformity of the coating sample; and a measurement device constructed to measure a parameter associated with the force required to remove the probe from the substrate after it has contacted the substrate.

21. The device of claim 20 further comprising a biasing element associated with the probe, constructed to be deflected as the probe is being moved to its spaced position by the force exerted by the coating on the probe.

22. The device of claim 21 wherein the measurement device is constructed to detect and measure the deflection of the biasing element.

23. The device of claim 22 wherein said measurement device is an LVDT.

24. The device of claim 21 wherein said biasing element is a leaf spring.

25. The device of claim 20 wherein said activation device comprises a motor to move said probe between its contact and spaced positions.

26. The device of claim 20 further comprising a computer to control movement of said probe.

27. The device of claim 20 wherein the area of said contact surface is less than about 10 mm$^2$.

28. The device of claim 20 wherein the area of said contact surface is less than about 5 mm$^2$.

29. The device of claim 20 wherein the area of said contact surface is less than about 1 mm$^2$.

30. The device of claim 20 wherein said activation device includes an electromagnet positioned above the probe, and the probe is moved to its contact position when no current is supplied to the electromagnet, and moved to its spaced position by magnetic force, when current is supplied to the electromagnet.

31. The device of claim 30, wherein the measuring device includes a light source and photosensor, positioned on opposite sides of the probe to detect the moment when the probe breaks free of the substrate, as the probe is being moved from the contact to the spaced position.

32. The device of claim 31 wherein the measuring device measures the current applied to the electromagnet at the point at which the probe breaks free of the substrate.

* * * * *

UNITED STATES PATENT AND TRADEMARK OFFICE
CERTIFICATE OF CORRECTION

PATENT NO.    : 6,050,139
DATED         : APRIL 18, 2000
INVENTOR(S)   : DOUGLAS W. BOUSFIELD, PHILLIP S. COLEMAN, JOHN C. HASSLER, AND ALONZO K. OSGOOD

It is certified that error appears in the above-identified patent and that said Letters Patent is hereby corrected as shown below:

On the title page, item:

[73] Assignee: please insert --University of Maine, Orono, Maine--.

Signed and Sealed this

Twelfth Day of September, 2000

Attest:

Q. TODD DICKINSON

*Attesting Officer*          *Director of Patents and Trademarks*